(12) United States Patent
Lee et al.

(10) Patent No.: US 6,440,443 B1
(45) Date of Patent: Aug. 27, 2002

(54) MICROENCAPSULATION FORMULATIONS OF CADUSAFOS

(76) Inventors: Fui-Tseng H. Lee, 38 Wittmer Ct., Princeton, NJ (US) 08540; Paul Nicholson, 615 Greenway Ave., Trenton, NJ (US) 08618; Janos Szamosi, 4 Baltusrol Ave., Washington, NJ (US) 07882; William T. Sommer, 1296 Oxford La., Union, NJ (US) 07083

(*) Notice: Subject to any disclaimer, the term of this patent is extended or adjusted under 35 U.S.C. 154(b) by 0 days.

(21) Appl. No.: 09/363,342

(22) Filed: Jul. 29, 1999

Related U.S. Application Data

(60) Provisional application No. 60/094,610, filed on Jul. 30, 1998.

(51) Int. Cl.$^7$ .............................................. A01N 25/28
(52) U.S. Cl. ...................... 424/408; 424/406; 514/109; 514/120; 514/121; 264/4.33
(58) Field of Search ................... 264/4.33; 424/405, 424/408, 417, 406, 490, 497; 274/109, 120, 121

(56) References Cited

U.S. PATENT DOCUMENTS

| | | | |
|---|---|---|---|
| 3,577,515 A | 5/1971 | Vandegaer | 424/32 |
| 4,107,292 A | 8/1978 | Nemeth | 424/78 |
| 4,876,290 A | * 10/1989 | Vivant | 521/76 |
| 4,938,797 A | 7/1990 | Hasslin et al. | 71/118 |
| 5,643,591 A | 7/1997 | Mehra et al. | 424/408 |

FOREIGN PATENT DOCUMENTS

| FR | 2591857 | 12/1986 | 25/28 |
|---|---|---|---|

* cited by examiner

*Primary Examiner*—Neil S. Levy

(57) ABSTRACT

Pesticidal formulations of cadusafos are provided. An aqueous capsule suspension is provided, containing from about 150 to about 360 grams of cadusafos per liter of formulation and having lower mammalian toxicity than aqueous cadusafos microemulsion formulations is prepared by interfacial polymerization of a first polyfunctional compound, such as a polymethylene polyphenyl isocyanate, with a second polyfunctional compound, such as a polyfunctional amine or mixtures of polyfunctional amines, in an aqueous phase optionally containing from about 0.05 to about 0.50 xanthan gum viscosity modifier/stabilizer. A granular form of the microencapsulated cadusafos is also provided. Several such formulations and the method of their preparation are described.

16 Claims, No Drawings

MICROENCAPSULATION FORMULATIONS OF CADUSAFOS

This Application claims the benefit of Provisional Application 60/094,610, filed Jul. 30, 1998.

FIELD OF THE INVENTION

The present invention relates to formulations of organophosphate pesticides. In particular, the invention provides microencapsulated formulations of the insecticide/nematicide, cadusafos, that are equally effective, yet reduced in toxicity, as compared with conventional formulations.

BACKGROUND OF THE INVENTION

The organophosphate compound, S,S-di-sec-butyl-O-ethyl phosphorodithioate (cadusafos), is an effective insecticide and nematicide. However, the toxicity of cadusafos impairs its safe use. For instance, a 100 g/l aqueous microemulsion formulation of cadusafos presently in commercial use recommends that the user wear complete body protection for handling and applying the formulation. The labeling also indicates that the formulation is highly toxic to mammals, fish, arthropods and birds.

Accordingly, a need exists to develop formulations of cadusafos that maintain its effectiveness as an insecticide or nematicide, but reduce its toxicity to mammals, birds, fish and other non-target organisms. Such formulations would improve safety to humans and would minimize any negative impact on the environment resulting from use of this compound.

SUMMARY OF THE INVENTION

Provided in accordance with the present invention are pesticidally effective, microencapsulated formulations of cadusafos having low or moderate toxicity to non-target organisms, among other advantages.

According to one aspect of the invention, the formulation comprises an aqueous suspension of microcapsules, which are composed of a polyurea shell surrounding a core of the cadusafos. The polyurea shell is formed from interfacial polymerization of a polyisocyanate and one or more polyfunctional amines, the polyurea. shell being sufficiently impenetrable to the cadusafos so as to effect the aforementioned reduction in mammalian toxicity of the formulation, as compared with known aqueous microemulsion cadusafos formulations of an equivalent or lesser cadusafos concentration.

According to another aspect of the invention, a granular cadusafos formulation is provided, which comprises the aforementioned microcapsules containing cadusafos affixed to a granular carrier.

Also provided in accordance with the present invention are processes for making the aforementioned aqueous capsule suspension (CS) or granular microencapsulated cadusafos formulations.

The microencapsulated cadusafos of the present invention possesses lower skin, oral, and inhalation toxicity to mammals, thereby enabling safer handling and use of the pesticide. According to United States Environmental Protection Agency ("EPA") guidelines, the formulations of the present invention are rated as Category II (warning) or Category III (caution) compositions at twice the concentration of non-microencapsulated liquid formulations of the same active ingredient, which are rated as Category II. The microencapsulated formulations exhibit no loss of pesticidal activity or physical and chemical stability as compared to non-microencapsulated formulations. In addition, the microencapsulated formulations of the present invention are consistent in color, which is not the case in aqueous microemulsion formulations of the compound if the technical cadusafos is pre-treated with copper salts to remove unpleasant odor for commercial use.

DETAILED DESCRIPTION OF THE INVENTION

The microencapsulated cadusafos of the invention is made according to the following basic steps: (a) providing an aqueous phase (also referred to herein as a "continuous" phase) containing an emulsifier and an antifoam agent; (b) providing a water-immiscible phase (also referred to herein as a "discontinuous" phase) containing the cadusafos along with a first polyfunctional compound; (c) emulsifying the aqueous phase with the water-immiscible phase to form a dispersion of water-immiscible droplets in the aqueous phase; and (d) adding to the dispersion, either neat or in an aqueous solution, a second polyfunctional compound, thus forming a polymeric shell known herein as a microcapsule, around the water-immiscible droplets; i.e., forming microcapsules of cadusafos The first polyfunctional compound is any suitable compound having two or more reactive groups, such as, but not limited to, an isocyanate monomer. The second polyfunctional compound is any suitable compound having two or more reactive groups, such as, but not limited to, a polyfunctional amine; wherein the first and second polyfunctional compounds are different. The suitability of the first and second polyfunctional compounds is that they have the ability to form a heteromeric structure at the interface between the dispersed cadusafos and the aqueous phase. Such compounds will include both hydrophobic and hydrophilic groups between the two compounds, such that such groups can both be in a single such compound or can be exclusive to one or the other such compound. The last step is referred to as interfacial polymerization due to the fact that the polyurea shell is formed by polymerization of the first and second polyfunctional compounds, which are preferably an isocyanate and a polyfunctional amine(s) at the interface of the water-immiscible phase (the droplets) and the aqueous phase, thereby forming, predferably, a polyurea shell.

Once the microcapsules are formed, the suspension is preferably cured, i.e., moderately heated to complete polymerization, after which one or more additives, such as propylene glycol, xanthan gum, urea, bactericides, amphoteric surfactants, inert dyes or ionic dispersing agents (e.g., alkyl naphthalene sulfonate), may be added.

The addition of materials after encapsulation and curing to adjust viscosity, stability and suspension/dispersion characteristics preferably do not affect the reduction of toxicity or the pesticidal efficacy of the formulation. A preferred further step comprises adjusting the pH of the formulation to neutral, i.e., from about pH 6.5 to about pH 7.5, which results in improved stability. The use of the modifier "about" with respect to pH is used herein to indicate a variance of at least one-half a pH unit, and preferably indicates a variance of one-half a pH unit. In other contexts herein where the modifier "about" is used to qualify a non-log unit, the "about" is intended to indicate a variance of ±15%, yet more preferably a variance of ±10%.

The aqueous phase ordinarily contains about 0.3 to about 3.0, preferably about 0.7 to about 2.5, weight percent of one or more emulsifiers. The emulsifier preferred for use in the present invention is polyvinyl alcohol. Other emulsifiers suitable for use in the present invention include, but are not limited to, nonylphenol ethoxylate, sorbitan mono- and trioleate, and ethoxylated oleate.

The aqueous phase also contains about 0.1 to about 1.0, preferably about 0.3 to about 0.9 weight percent of one or more antifoam agents. Antifoam agents suitable for use in the present invention include, but are not limited to, silicon based antifoam agents such as Dow Corning Antifoam DC1500 and DC1520.

The aqueous phase optionally may also include a viscosity modifier/stabilizer, such as xanthan gum from about 0.05 to about 0.50, preferably about 0.06 to about 0.40, weight percent, as well as one or more bactericides from about 0.02 to about 0.10, preferably about 0.03 to about 0.05, weight percent. Bactericides useful for the present invention include, but are not limited to, Legend MK (Rohm & Haas Co.), Proxel GXL (Zeneca, Inc.) and Dowicide A (Dow Chemical).

The water-immiscible phase (also referred to in the examples as the polyisocyanate solution) ordinarily contains from about 50 to about 98, preferably about 53 to about 92 weight percent cadusafos and about 2 to about 35, preferably about 4 to about 25, weight percent of the first polyfunctional compound, preferably an isocyanate monomer. Polymethylene polyphenyl isocyanate (PMPPI) is particularly preferred for use in the present invention; e.g., Mondur MR (Miles, Inc.), Papi 27 or 135 (Dow Chemical) and Desmodur (Bayer). Other suitable first polyfunctional compounds can also be used in accordance with the invention, provided they possess appropriate chemical and physical characteristics (e.g., chain length, functionality) such that the polymeric shell formed around the cadusafos acts as a barrier to egress of the cadusafos from the microcapsules. Appropriate first polyfunctional compounds will be apparent to persons skilled in the art.

The water-immiscible phase also may contain a hydrocarbon solvent, such as, for example, a vegetable oil. However, the solvent is optional in the preparation of microcapsule formulations of cadusafos, particularly with respect to such formulations containing more than about 240 grams cadusafos per liter. Hydrocarbon solvents useful in the practice of the present invention include, but are not limited to, petroleum hydrocarbons such as Aromatic 200, Aromatic 150 and Exxate 1000 (all from Exxon Chemicals), or vegetable oils, such as corn oil. The solvent, if any is used, is present at about 15 to about 30, preferably about 20 to about 25, weight percent of the water-immiscible phase.

One advantage of the present invention is that the formulations can be prepared with either untreated cadusafos or with cadusafos that has been treated with a copper salt. Copper salts are added to cadusafos to reduce its odor. Typically, copper salts interfere with the formation of microcapsules by interfacial polymerization, but this is found not to be the case in the present process.

The second polyfunctional compound solution ordinarily contains about 10 to about 100, preferably about 20 to about 70, weight percent of a second polyfunctional compound or mixture of such second polyfunctional compounds. Examples of suitable second polyfunctional compounds that are useful for practice of the present invention include various polyfunctional amines, such as, but not limited to: diethylenetriamine (DETA), triethylenetetramine (TETA), and 1,6-hexanediamine (HDA).

Interfacial polymerization of the first and second polyfunctional compounds forms the polymeric microcapsules surrounding the cadusafos according to the following exemplary chemistry using PMPPI as the first polyfunctional compound and a generic amine for the second polyfunctional compound:

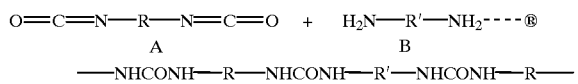

Wherein A is PMPPI with an average functionality of about 2.3 to about 2.6 and B is a polyfunctional amine.

Several parameters of the process of the invention contribute to the characteristics of the final formulation. The emulsification step preferably is effected using high shear mixing to yield small droplets of the immiscible phase. The average size of the microcapsules of the invention is about 5 to about 25 $\mu$m. Factors that influence the size of the microcapsules, as well as the stability of the emulsion, include: (1) total amount of shear applied during the emulsification; (2) type and amount of surfactant or hydrocarbon solvent in the discontinuous phase, if any are used; (3) temperature or viscosity of the mixture; and (4) presence and amount of xanthan gum or alkyl naphthalene sulfonate dispersing agent in the mixture, if any.

Selection of relative percentages of first and second polyfunctional compound monomers (e.g., PMPPI and amines) in the discontinuous phase to achieve the appropriate microencapsulation requires a balance among competing factors. In general, increasing the percentage of the monomers in the discontinuous phase decreases toxicity of the final formulation. Likewise, decreasing the percentage of monomers results in higher toxicity of the final formulation. In an optimum general formulation of the invention, a balance of high efficacy and low toxicity is achieved by including about 5 to about 35, preferably about 7 to about 30, weight percent of monomers in the discontinuous phase. The operating conditions needed to yield microcapsules from the appropriate monomer concentrations depends upon the emulsifying equipment used; the determination of such conditions is well within the level of skill in the art.

In contrast to the vigorous conditions needed for the emulsification step, agitation during addition of the second polyfunctional compound should be low-shear, as accomplished through use of a mechanical paddle stirrer. After the second polyfunctional compound has been added, stirring is continued while the suspension is cured, e.g., by heating to a temperature of about 20 to about 60° C., preferably from about 30 to about 50° C., for about one to about 10 hours, preferably about three to about four hours.

One or more substances may be added to the formulation after encapsulation is complete. These typically are selected from the following, though other substances not specifically listed will be apparent to persons skilled in the art (1) propylene glycol, preferably from about 1.3 to about 6.0 weight percent; (2) urea, preferably from about 5.0 to about 5.5 weight percent; (3) xanthan gum, preferably from about 0.003 to about 0.30 weight percent; (4) one or more bactericides to a total weight percent of about 0.01 to about 0.10; (5) one or more inert dyes at a total weight percent up to about 0.05; and (6) one or more surfactants up to a total weight percent of about 7.0; each weight percent relative to the weight of the formulation after addition of the additives.

The preferred practice, after curing the microcapsules, is to neutralize the formulation, e.g., with phosphoric, acetic or hydrochloric acid, although other acids will suffice. The post-encapsulation additives are then added, and stirring of the formulation continued for about four hours at a moderately heated temperature (e.g., 50° C.).

Capsule Suspension (CS) formulations of cadusafos prepared by the above-described methods have the following general compositional features: they contain from about 150 to about 360 grams cadusafos per liter of formulation, and comprise an aqueous suspension of microcapsules made up of a polyurea shell surrounding a core of cadusafos and, optionally, a hydrocarbon solvent, and further comprise an emulsifier, such as about 0.3 to about 3.0 weight percent polyvinyl alcohol, and an antifoam agent at about 0.05 to about 0.5 weight percent. The formulation also may optionally contain about 0.06 to about 0.4 weight percent xanthan gum or other viscosity modifier/stabilizer, about 0.02 to about 0.10 weight percent of one or more bactericides, about 0.7 to about 6.7 weight percent of one or more surfactants, and about 1.2 to about 5.8 weight percent of propylene glycol or urea, or a combination thereof. Preferred formulations contain about 200 g/l cadusafos,-comprising about 53 to about 92 weight percent cadusafos and about 4 to about 25 weight percent PMPPI in the water-immiscible phase, and utilizing DETA, TETA or HDA as the polyfunctional amine.

In another aspect of this invention, the above-described CS cadusafos formulations are used to prepare granular microemulsion (G-ME) formulations of cadusafos. The G-ME formulations are prepared by the following steps: (a) provide a homogeneous mixture of the microencapsulated or capsule suspension (CS) cadusafos formulation and an adhesive agent; b) disperse the mixture onto a carrier; and c) allow the carrier to dry, thereby forming the granular formulation.

The G-ME formulation will ordinarily contain about 5.0 to about 30.0, preferably about 10.0 to about 20.0, weight percent of cadusafos CS formulation, about 60.0 to about 95.0, preferably about 70.0 to about 80.0, weight percent of a carrier, and about 0.05 to about 5.0, preferably about 0.1 to about 2.0, weight percent of an adhesive agent.

Adhesive agents useful for the practice of the invention include, but are not limited to, calcium and sodium lignosulfonates, polyalkylene glycols, and other polymer solutions, such as resins. Other suitable adhesives will be readily apparent to persons of skill in the art.

Examples of carriers that may be used in the present invention include, but are not limited to, cellulose complexes, attapulgite clays, silica complexes, and plant materials, such as corn cobs. Other suitable carriers will be readily apparent to persons of skill in the art.

The time required for the mixture of the CS formulation and the adhesive to reach homogeneity is not critical, but is usually from about one to about ten minutes. Dispersion onto the carrier continues until the entire mixture is exhausted. The granular formulation is then dried for several hours.

The following examples are provided to illustrate embodiments of the invention. They are not intended to limit the invention in any way.

EXAMPLE 1

Preparation of a 200 g/l Cadusafos Capsule Suspension (CS) Formulation (Formulation PP)

A stock solution of aqueous 20% (wt/wt) partially hydrolyzed polyvinyl alcohol (Airvol® 203) was prepared by stirring and heating the appropriate amounts of polyvinyl alcohol and water at about 80–90° C. for one hour. The cooled solution was stored for later use.

The aqueous phase for microencapsulation was prepared in a four-liter stainless steel beaker by mixing 92 g of the aqueous 20% polyvinyl alcohol solution, 68.6 g of aqueous 2% xanthan gum (Keizan® S), and 8.2 g of polydimethyl siloxane antifoam agent (Dow Corning® 1520) in 1832 g water. Then 332.5 g of this mixture was transferred to a one-liter beaker. The mixture was mixed for one minute at high speed, then a pre-blended solution of 140.0 g of cadusafos (treated previously with 2.5% copper naphthenate), 60.0 g of petroleum solvent (a mixture of $C_9$–$C_{15}$ aromatic, naphthalene-depleted, hydrocarbons, flash point 95° C., Aromatic 200 ND), and 43.0 g of PMPPI (Mondur® MR) was added rapidly, and the mixture was emulsified for one minute. The mixture was then placed in a one-liter 3-necked roundbottom flask equipped with a mechanical stirrer, and 27.0 g of a 70% aqueous solution of HDA in 10.0 g water was added during a 30 second period. Upon completion of the addition, the mixture was heated to 50° C. and held for four hours. After this time, the mixture was cooled to 30° C. and 35.0 g urea was added, followed by 25.0 g aqueous 2% xanthan gum (Kelzan® S). The formulation was then mixed gently for about one hour and stored. The formulations described in Tables 1 and 2 were prepared in this manner.

EXAMPLE 2

Large Scale Preparation of a 200 g/l Cadusafos Capsule Suspension (CS) Formulation (Formulation PB-8PG)

A solution of 2.09 pounds of a polyvinyl alcohol, 0.16 pound of aqueous 2% xanthan gum, 0.9 pound of a polydimethyl siloxane antifoam agent, 7.62 pounds of a sodium salt of an alkyl naphthalene sulfonate, and 0.07 pound of a 1,2-benzisothiazolin-3-one bactericide in 226.2 pounds of water was placed in a 120 gallon stainless steel vessel, and stirred at 80° C. for one hour. After this time, the solution was cooled to 20° C. and placed in a 120 gallon stainless steel batch homogenizer. The homogenizer was allowed to reach a speed of about 3,500 rpm, and then a pre-blended solution of 82.6 pounds of cadusafos technical (which was pre-treated with 2.1 pounds of copper naphthenate) and 15.1 pounds of PMPPI was fed at 10 psi into the homogenizer. The mixture was homogenized for about one minute. Upon completion of homogenization, the mixture was quickly dropped into a 100 gallon stainless steel reactor with angle dual propeller agitation. An amine mixture consisting of 9.4 pounds of 70% aqueous HDA solution in 4.4 pounds of water was added rapidly. After the amine addition was complete, the mixture was vigorously stirred for ten minutes and then heated to 50° C. where it cured for three to four hours with slow mixing. At the end of the curing period, the mixture was cooled to 35° C. and then neutralized to a pH of 6.5 to 7.5 with 2.2 pounds of concentrated phosphoric acid. Upon completion of addition, 15.51 pounds of aqueous 2% xanthan gum, 22.0 pounds of propylene glycol, 0.14 pounds of a 1,2-benzisothiazolin-3-one bactericide, and 0.81 pounds of a polydimethyl siloxane antifoam agent were added to the formulation. The formulation after mixing for one hour had a viscosity of 325 cps and a suspensibility of 98%.

EXAMPLE 3

Large Scale Preparation of a 200 g/l Cadusafos Capsule Suspension (200 CS) Formulation (Formulation PB-C14U-ND)

To a stirred solution of 7.24 pounds of a polyvinyl alcohol, 0.32 pound of aqueous 2% xanthan gum, 3.33 pounds of a polydimethyl siloxane antifoam agent (Dow Coming® 1520), 7.53 pounds of a sodium salt of an alkyl naphthalene sulfonate, and 0.20 pound of a 1,2-benzisothiazolin-3-one bactericide in 391.3 pounds of water in a 120 gallon stainless steel batch homogenizer was added a pre-blended solution of 172.6 pounds of cadusafos technical (which was pre-treated with 4.21 pounds of copper naphthenate), 53.0 pounds of PMPPI, and 74.1 pounds of a petroleum solvent (a mixture of $C_9$–$C_{15}$ aromatic, naphthalene-depleted, hydrocarbons, flash-point 95° C.). Upon completion of addition, the mixture was stirred at a speed of about 3,500 rpm for about ten minutes in the homogenizer. Upon completion of homogenization, an amine mixture consisting of 33.3 pounds of a 70% aqueous solution of HDA in 12.3 pounds of water was added rapidly. After the amine addition was complete, the mixture was agitated for ten minutes and then heated to 50° C. where it cured for three to four hours. At the end of the curing period, the mixture was cooled to 35° C. and then neutralized to a pH of 6.5 to 7.5 with 7.47 pounds of 85% phosphoric acid. Upon completion of addition, 32.04 pounds of aqueous 2% xanthan gum, 44.6 pounds of urea, and 0.17 pound of an inert dye (Tricon Green 18800) were added to the formulation. The formulation was then mixed for one hour and stored.

EXAMPLE 4

Large Scale Preparation of a 200 g/l Cadusafos Capsule Suspension (200 CS) Formulation (Formulation PB-C14U-ND)

To a 14.6 pound per minute stream of a stirred solution of 1.77% of a polyvinyl alcohol, 0.08% of xanthan gum, 0,81% of a polydimethyl siloxane antifoam agent (Dow Coming® 1520), 1.84% of a sodium salt of an alkyl naphthalene sulfonate (Lomar® LS-1), 0.05% of a 1,2-benzisothiazolin-3-one bactericide (Proxel® GXL) and 95.46% of water was combined a 10.9 pound per minute stream of pre-blended solution of 57.55% of cadusafos technical, 17.75% of PMPPI, and 24.70% of a petroleum solvent (a mixture of $C_9$–$C_{15}$ aromatic, naphthalene-depleted, hydrocarbons, flash-point 95° C.). The combined stream was fed through an in-line homogenizer producing adequate sheer to obtain desired particle size. To the homogenizer discharge stream was fed a 1.6 pound per minute amine mixture stream consisting of 73% of an aqueous 70% HDA solution in 27% of water, and the resulting stream fed into a agitated reactor set at 35° C. The mixture was continuously discharged from the reactor to a second 1000 gallon reactor while maintaining a constant residence time of 20–30 minutes. When the second 1000 gallon reactor was filled (5420 pounds), the mixture was heated to 50 ° C. where it was cured for three to four hours. At the end of the curing period, the mixture was cooled to 35° C. and then neutralized to a pH of 6.5 to 7.5 with 75.0 pounds of 85% phosphoric acid. Upon completion of addition, 230.6 pounds of aqueous 2% xanthan gum, 321.6 pounds of urea, and 1.3 pounds of an inert dye (Tricon Green 18800) were added to the formulation. The formulation was then mixed for one hour, filtered and stored. The formulations described in Tables 3 and 4 were prepared in the manner of Examples 2, 3, and 4.

EXAMPLE 5

Preparation of a 3% Weight/Weight Cadusafos Granular Microencapsulated (3G-ME) Formulation In a one liter beaker were placed 83.0 grams of the cadusafos 200 CS formulation prepared as described above, and 10.0 grams of a calcium lignosulfonate (Norlig® A). The mixture was mixed until it was homogenous (about ten minutes) and then sprayed into a commercially available tumbler/blender containing 417 grams of a cellulose complex consisting of paper filler, kaolin clay, calcium carbonate, and titanium dioxide (Biodac® 20/50) until the entire mixture had been exhausted. Upon complete exhaustion of the mixture, the tumbling/blending was stopped and the formulation was allowed to air-dry for about 16 hours.

EXAMPLE 6

Toxicity Studies

Laboratory tests which show the reduced mammalian dermal toxicity of the cadusafos capsule suspension (CS) formulations were carried out in the following manner. For each formulation to be tested (referred to as the test material), six Sprague-Dawley rats (3 males and 3 nulliparous, nonpregnant 30 females) were treated with the cadusafos CS formulation at dosage levels of 50, 200, 400, and 2000 mg/Kg. On the day before the test materials were applied, the trunk of each rat was clipped free of hair to expose at least 10% of the rat's body surface. The test materials were applied to a 4-ply 2×2 inch gauze pad, which was secured on the rat test site. A self-adhesive, elastic bandage, lined with plastic, was wrapped around the trunk of the rat to ensure that the test material remained in contact with the skin. After approximately twenty-four hours, the wrapping and pads were removed and any residual test material was wiped away with a clean gauze pad moistened with tap water. Observations for mortality were conducted twice daily. The animals were observed approximately 3 hours after dosing on Day 0 and daily thereafter for 14 days. The nature, onset and duration of all gross or visible toxicological or pharmacological effects were recorded daily, with the exception of local irritation on the test site. The time of death (or the discovery of death) was also noted. The body weights of the rats were recorded prior to dosing and on days 7 and 14. Those animals failing to survive the observation period were weighed as soon as possible after discovery of death. Necropsies were performed on all of the animals that died during the tests. All animals surviving the observation period (Day 14) were sacrificed and examined grossly. All internal abnormalities were recorded. $LD_{50}$'s were approximated from the dosage levels. The tests results, shown in Table 5, indicate that the CS formulations of the present invention are effective in reducing the mammalian dermal toxicity of the cadusafos. While all the formulations showed reduced dermal toxicity, Formulations K, KK, LL, MM, PB-9PG, and PB-11PG reduced the toxicity to Category III, and Formulation PB-14U-ND reduced the toxicity to Category IV. See below for definitions of Categories I–IV.

Laboratory tests which show the reduced mammalian oral toxicity of the cadusafos capsule suspension (CS) formulations were carried out in a similar manner to that described above. The tests differed in that the test materials were administered by oral intubation, using a ball-tipped intubation needle, at dosage levels of 25, 50, 200 and 500 mglkg rather than 50, 200, 400, and 2000 mg/kg, and that the rats were starved for about 18 hours prior to testing. The tests results, shown in Table 6, indicate that the CS formulations of the present invention are effective in reducing the mammalian oral toxicity of the cadusafos. While all the formulations showed reduced oral toxicity, Formulations B, PP, Q, and PB-14U-ND reduced the toxicity to Category III.

Formulations PB-8PG and PB-C14U-ND were also tested for reduced mammalian inhalation toxicity in the following manner. Six Sprague-Dawley rats (3 males and 3 nulliparous, nonpregnant females) were exposed for four hours to an atmosphere of the test material in an 11-liter nose-only inhalation chamber operated under dynamic airflow conditions. The concentration level of the test material was >0.5 mgA and >0.05 mg/l. Observations for toxicity and mortality were made hourly during the exposure period, upon removal from the chamber, and at least once daily during 14 days thereafter. Individual body weights were recorded prior to exposure (Day 0) and on Days 7 and 14. Those animals failing to survive to the end of the observation period were weighed as soon as possible after discovery of death. Necropsies were performed on all animals which died during the study. All animals surviving at Day 14 were anesthetized and sacrificed prior to gross examination. All internal abnormalities were recorded. The results of the inhalation study indicated that Formulations PB-8PG and PB-C14U-ND had estimated four-hour LC50's greater than 1.04 mg/l and 3.87 mg/l, respectively. These data show that the inhalation toxicity is reduced from a Category I to a Category III. The rat acute inhalation of a known cadusafos 100 ME formulation (100 g/l cadusafos aqueous microemulsion) is 0.026 mg/l/4 hours. The terms "Category I", "Category II", "Category III" and "Category IV" refer to the category the EPA assigns to a chemical compound based on its toxicity. The criteria for classifying a compound as "Category I", "Category II", "Category III" or "Category IV" are the following:

| Hazard Indicators | Category I | Category II | Category III | Category IV |
|---|---|---|---|---|
| Oral LD50 | Up to and including 50 mg/kg | >50 thru 500 mg/kg | >500 thru 5000 mg/kg | >5000 mg/kg |
| Dermal LD50 | Up to and including 200 mg/kg | >200 thru 2000 mg/kg | >2000 thru 5000 mg/kg | >5000 mg/kg |
| Inhalation LC50 (Actual) chamber concentration measure for a 4 hour exposure | Up to and including 0.05 mg/L | >0.05 thru 0.5 mg/L | >0.5 thru 5 mg/L | >5 mg/L |

EXAMPLE 7

Efficacy Studies

Generally formulations of the present invention have been found to be effective against a number of pests. The following procedures are representative of the efficacy of the formulations of the present invention and are not intended to limit the scope of the invention in any manner.

Formulations AA to FF, excluding DD, were tested for efficacy and persistence in soil for controlling root-knot nematode (RKN), Meloidogyne incognita, on tomato. A three-week old tomato (Lycopersicon esculentum, var "Rutgers") was planted in a 10 cm square pot containing a nonsterile 50:50 sand:soil mixture. Ten replicate pots (five replicates for two sets of tests) were prepared for each rate of application of test formulation. Stock dispersions of each of the test formulations were prepared by dispersing a sufficient amount of test material in 100 ml of water to give rates of application of 0.25, 0.5, 1, and 2 kg a.i./ha. Each pot received 10 ml of the appropriate suspension on the surface immediately around the tomato, and a control treatment for each of the two experimental set of pots received only water.

Pots were also prepared as above with the same rates of the 100 ME cadusafos formulation and technical cadusafos. The RKN eggs used in the experiment were separated from a gelatinous matrix by vigorously shaking the roots of heavy galled tomato plants for four minutes in a 1% aqueous sodium hypochlorite solution. The resulting egg suspension was rapidly poured through nested 60, 325, and 500 mesh sieves. The eggs were collected on the 500 mesh sieve and gently rinsed with water to remove any excess sodium hypochlorite. The eggs were taken up in water, and the resulting aqueous suspension was appropriately diluted with water to give about 2000 eggs per plant which results in an effective inoculant level of about 1000 infective larvae per pot. The eggs were counted using a dissecting microscope. All the pots were infested with nematodes by pippetting the inoculum into the openings around the roots of the previously treated tomato transplants. Pots infested with nematodes 48 hours after soil treatment, hereafter referred to as "set 1". Pots for examination of residual activity, hereafter referred to as "set 2", were treated and maintained in the greenhouse for seven days prior to nematode infestations. Upon nematode infestation, the pots were maintained in the greenhouse for 28 days and monitored for phytotoxicity symptoms. At the conclusion of the 28 day period, the soil was washed away from the tomato plants roots and rated according to the following scheme:

| Gall Rating | Description |
|---|---|
| 0 | Complete and healthy root system no infestation. |
| 1 | Very few small galls can be detected upon close examination. |
| 2 | Small root galls as in "1", but more numerous and easily detected. |
| 3 | Root system is characterized by numerous small galls, some of which may have grown together, but function of the roots is not yet seriously affected. |
| 4 | In addition to numerous small galls, some big galls are present, but the majority of the roots are still functioning. |
| 5 | About 25% of the root system is out of function due to severe galling. |
| 6 | Up to 50% of the root system is out of function due to severe galling. |
| 7 | About 75% of the root system is heavily galled and lost for production. |
| 8 | No healthy roots are left, the nourishment of the plant is interrupted, but the plant is still green. |
| 9 | The completely galled root system is rotting, the plant is dying. |
| 10 | Plant and roots are dead. |

The test results shown in Tables 7 and 8 indicate that all of the cadusafos CS formulations were effective in controlling nematodes on tomatoes and there no clear differences among the formulations. In Table 7, only the data for the two lower rates of application are shown because all treatments completely controlled the nematodes at 1 and 2 kg a.i./ha.

Formulations B, E, F, G, and H were tested against southern corn rootworm (SCR) larvae to determine the initial and residual soil activity of the cadusafos CS formulations. Each formulation was evaluated using three 5000 gram replicates of two types of soil (clay soil and sandy loam soil). The sandy loam soil consisted of 30% clay, 30% sand, and 3% organic material while the clay loam soil consisted of 87% sand, 3% clay, and 0.9% organic material.

Prior to treatment, the soils were placed in a five gallon bucket, air dried, and then adjusted to 50% soil moisture holding capacity. Each formulation was sprayed at 20 psi onto the sifted soil at rates of application of 0.1, 0.2, 0.5 and 1.5 ppm in the sandy-loam soil and 0.1 and 0.2 ppm in the clay loam soil. Buckets of the two types of soil were also sprayed as above with the same rates of the cadusafos 100 ME formulation. Upon treatment, the soil was mixed for five minutes and then transferred to a 2.84 liter container. The soil was covered and then maintained at 26° C. and 40–50% soil moisture in the green house until it was needed for testing. At each sampling period, 50 grams of the treated soil was added to a 113.4 grams plastic cup containing two kernels of two day old germinated corn seeds, which completely covered the seeds. Fifteen late second-instar SCR larvae were added to each cup. Each cup was covered with a tight fitting lid and placed in an environmental chamber held at 24–26° C. After 96 hours, 226.8 grams paper cups corresponding to each soil container were filled to a depth of approximately 1.27 cm. with soapy water. A funnel with a plastic mesh screen in the bottom was placed in each paper cup. Each 50 gram increment of extracted soil was then placed into the funnel in the corresponding paper cup. The soil remained in the funnel until completely dry, and all live larvae had crawled down into the cup below. The number of SCR larvae in the bottom of the cup were recorded as alive. From these data, the percent mortality was determined in each soil sample.

The results of the tests indicate that the cadusafos CS formulations of the present invention were equal to or slightly more active residually than the cadusafos 100 ME formulation. For example, at 0.2 ppm in clay loam soil, Formulation G caused 97% mortality 84 days after treatment while the cadusafos 100 ME formulation caused 40% mortality. These data are presented in Tables 9 and 10.

The present invention is not limited to the embodiments described herein, but may be varied and modified within the scope of the appended claims. Such variation includes, but is not limited to, mixtures of one or more pesticides, whether encapsulated or not, in which the microencapsulated cadusafos of the invention is part of the mixture.

TABLE 1

Preparation of Cadusafos Capsule Suspension (CS) Formulations
(Components and Amounts)

| Formulation (grams/L) | Weight (grams) | | | | | | | | | | |
|---|---|---|---|---|---|---|---|---|---|---|---|
| | A (240) | B (200) | C (180) | D (200) | E (200) | E-1 (200) | E-2 (200) | F (200) | G (240) | H (220) | J (270) |
| Component | | | | | | | | | | | |
| Aqueous Solution | | | | | | | | | | | |
| Water | 430.7 | 430.7 | 430.7 | 316.0 | 394.1 | 1182.3 | 2364.6 | 394.1 | 394.1 | 394.1 | 394.1 |
| PVA | 4.0 | 4.0 | 4.0 | 4.0 | 3.98 | 11.94 | 23.88 | 3.98 | 3.98 | 3.98 | 3.98 |
| Xanthan Gum | 0.3 | 0.3 | 0.3 | — | 0.28 | 0.84 | 1.68 | 0.28 | 0.28 | 0.28 | 0.28 |
| Antifoam | 1.8 | 1.8 | 1.8 | 1.8 | 1.64 | 4.92 | 9.84 | 1.64 | 1.64 | 1.64 | 1.64 |
| Isocyanate Solution | | | | | | | | | | | |
| Cadusafos | 170.0 | 140.0 | 140.0 | 140.0 | 140.0 | 420.0 | 840.0 | 140.0 | 140.0 | 140.0 | 140.0 |
| Petroleum Solvent | — | 30.0 | 30.0 | 30.0 | 30.0 | 90.0 | 180.0 | 30.0 | 30.0 | 30.0 | — |
| PMPPI | 36.0 | 30.0 | 30.0 | 30.0 | 30.0 | 90.0 | 180.0 | 15.0 | 7.5 | 12.0 | 30.0 |
| Amine Solution | | | | | | | | | | | |
| TETA | 19.0 | 19.0 | 19.0 | 19.0 | — | — | — | — | — | — | — |
| DETA | — | — | — | — | 19.0 | 57.0 | 114.0 | 9.5 | 4.75 | 7.22 | 8.5 |
| Water | 31.0 | 31.0 | 31.0 | 31.0 | 31.0 | 93.0 | 186.0 | 15.5 | 7.75 | 11.78 | — |
| Post Encapsulation Stabilizers | | | | | | | | | | | |
| Propylene Glycol | — | — | 9.3 | 9.3 | 9.0 | 27.0 | 54.0 | 9.0 | 9.0 | 9.0 | 9.0 |
| Xanthan Gum | 0.03 | 0.02 | 1.0 | 1.0 | 1.0 | 3.0 | 6.0 | 1.0 | 1.0 | 1.0 | 1.0 |
| Water | 1.47 | 0.98 | — | — | — | — | — | — | — | — | — |
| Con. $H_3PO_4$ | — | — | 18.0 | — | 18.0 | 54.0 | 108.0 | 11.0 | — | 4.0 | — |
| Con. HCl | — | — | — | 15.5 | — | — | — | — | — | — | 11.9 |
| Na Sulfonate | — | — | — | — | 5.0 | 15.0 | 30.0 | 5.0 | 5.0 | 5.0 | 5.0 |
| Bactericide A | — | — | — | — | 0.3 | — | 1.8 | 0.3 | 0.3 | 0.3 | — |

| Formulation (grams/L) | Weight (grams) | | | | | | | | | |
|---|---|---|---|---|---|---|---|---|---|---|
| | K (200) | L (240) | M (240) | N (240) | O (240) | P (250) | Q (250) | R (250) | S (250) | T (250) |
| Component | | | | | | | | | | |
| Aqueous Solution | | | | | | | | | | |
| Water | 207.06 | 281.01 | 319.8 | 319.8 | 325.38 | 261.29 | 239.6 | 261.29 | 239.6 | 288.6 |
| PVA | 19.32 | 2.62 | 8.76 | 8.76 | 3.04 | 2.44 | 2.23 | 2.44 | 2.23 | 2.23 |
| Xanthan Gum | 1.45 | 0.2 | 0.21 | 0.21 | 0.23 | 0.18 | 0.17 | 0.18 | 0.17 | 1.17 |
| Antifoam | 8.61 | 1.17 | 1.23 | 1.23 | 1.35 | 1.09 | 1.0 | 1.09 | 1.0 | 1.0 |
| Isocyanate Solution | | | | | | | | | | |
| Cadusafos | 840.0 | 140.0 | 140.0 | 140.0 | 170.0 | 140.0 | 140.0 | 140.0 | 140.0 | 140.0 |

TABLE 1-continued

Preparation of Cadusafos Capsule Suspension (CS) Formulations
(Components and Amounts)

| | | | | | | | | | | |
|---|---|---|---|---|---|---|---|---|---|---|
| Petroleum Solvent | 180.0 | — | — | — | — | — | — | — | — | — |
| PMPPI | 180.0 | 15.0 | 15.0 | 15.0 | 15.0 | 15.0 | 24.0 | 15.0 | 24.0 | 24.0 |
| Amine Solution | | | | | | | | | | |
| DETA | 114.0 | 10.0 | 9.5 | 9.5 | 9.5 | 9.5 | 15.6 | 5.7 | 14.44 | 14.44 |
| Water | 186.0 | — | 15.5 | 15.5 | 15.5 | 15.5 | 25.4 | 9.3 | 23.56 | 23.56 |
| Post Encapsulation Stabilizers | | | | | | | | | | |
| Propylene Glycol | 60.0 | 28.0 | 28.0 | 28.0 | 28.0 | 28.0 | 28.0 | 28.0 | 28.0 | 28.0 |
| Xanthan Gum | 6.0 | 1.0 | 1.0 | 1.0 | 1.0 | 1.0 | 1.0 | 1.0 | 1.0 | — |
| Water | 294.0 | 49.0 | — | — | — | 49.0 | 49.0 | 49.0 | 49.0 | — |
| Con. $H_3PO_4$ | 99.0 | 11.0 | 11.0 | 6.84 | 6.84 | 8.5 | 11.4 | 2.5 | 11.4 | 11.4 |
| Na Sulfonate | 30.0 | 5.0 | 5.0 | 5.0 | 5.0 | 5.0 | 5.0 | 5.0 | 4.0 | 4.0 |
| Bactericide A | 1.0 | 0.3 | 0.3 | 0.3 | 0.3 | 0.3 | 0.3 | 0.3 | 0.3 | 0.3 |
| Amphoteric Surfactant | — | 15.0 | — | — | — | — | — | — | — | — |

| | Weight (grams) | | | | | | | | | |
|---|---|---|---|---|---|---|---|---|---|---|
| Formulation (grams/L) | U (250) | V (250) | W-1 (360) | W-2 (360) | W-3 (360) | X (250) | Y (250) | Z (250) | AA (250) | BB (200) | BB-1 (200) |
| Component | | | | | | | | | | | |
| Aqueous Solution | | | | | | | | | | | |
| Water | 264.1 | 261.14 | 270.42 | 270.42 | 270.42 | 261.14 | 261.22 | 261.29 | 251.42 | 374.68 | 384.54 |
| PVA | 2.23 | 2.21 | 5.0 | 5.0 | 5.0 | 2.21 | 2.35 | 2.44 | 2.35 | 3.5 | 3.59 |
| Xanthan Gum | 0.67 | 0.67 | 0.22 | 0.22 | 0.22 | 0.67 | 0.38 | 0.18 | 0.18 | 0.26 | 0.27 |
| Antifoam | 1.0 | 0.98 | 2.28 | 2.28 | 2.28 | 0.98 | 1.05 | 1.09 | 1.05 | 1.56 | 1.6 |
| Na Sulfonate | — | — | — | — | — | — | — | 5.0 | 5.0 | 5.0 | 5.0 |
| Isocyanate Solution | | | | | | | | | | | |
| Cadusafos | 140.0 | 140.0 | 289.8 | 289.8 | 289.8 | 140.0 | 140.0 | 140.0 | 140.0 | 140.0 | 140.0 |
| Petroleum Solvent | — | — | 31.2 | 31.2 | 31.2 | — | — | — | — | — | — |
| PMPPI | 24.0 | 15.0 | 62.5 | 62.5 | 62.5 | 15.0 | 15.0 | 15.0 | 15.0 | 15.0 | 12.0 |
| Cu naphthalene | — | — | — | — | — | — | — | — | 1.4 | 0.7 | 0.7 |
| Amine Solution | | | | | | | | | | | |
| DETA | 14.44 | 9.5 | 25 | 25 | 25 | 9.5 | 9.5 | 9.5 | 9.5 | 9.5 | 0.4 |
| Water | 23.56 | 15.5 | — | — | — | 15.5 | 15.5 | 15.5 | 15.5 | 15.5 | 19.6 |
| Post Encapsulation Stabilizers | | | | | | | | | | | |
| Propylene Glycol | 28.0 | 28.0 | — | — | 40.0 | 28.0 | 28.0 | 28.0 | 28.0 | 35.0 | 35.0 |
| Xanthan Gum | — | 0.5 | 0.52 | 0.52 | 0.52 | 0.5 | 0.5 | 0.5 | 0.7 | 0.7 | 0.7 |
| Water | — | 24.5 | 25.68 | 25.68 | 25.68 | 24.5 | 24.5 | 24.5 | 34.3 | 34.3 | 34.3 |
| Con. $H_3PO_4$ | 11.4 | 8.5 | — | — | — | — | — | — | — | — | — |
| Con. HCl | — | — | 16.0 | 16.0 | 16.0 | 22.0 | 11.8 | 10.4 | 12.0 | 12.0 | 12.0 |
| Na Sulfonate | 4.0 | 5.0 | 54.4 | 54.4 | 59.4 | 12.5 | 12.5 | 7.5 | 7.5 | 7.5 | 7.5 |
| Bactericide A | — | 0.3 | — | — | — | — | — | — | — | — | 13 |
| Bactericide B | — | — | — | — | 0.4 | 0.3 | 0.3 | 0.3 | 0.3 | 0.3 | 0.3 |
| Amphoteric Surfactant | — | 25.0 | — | 26.0 | 26.0 | — | — | — | — | — | — |
| Antifoam | — | — | — | — | 2.02 | — | — | — | — | — | — |

| | Weight (grams) | | | | | | | | | |
|---|---|---|---|---|---|---|---|---|---|---|
| Formulation grams/L | CC (150) | DD (150) | EE (200) | FF (200) | GG (200) | HH (200) | JJ (200) | KK (200) | LL (200) | MM (200) | NN (200) |
| Component | | | | | | | | | | | |
| Aqueous Solution | | | | | | | | | | | |
| Water | 606.39 | 591.6 | 354.96 | 374.68 | 374.68 | 374.68 | 369.77 | 1109.26 | 1123.22 | 1123.22 | 1123.22 |
| PVA | 5.66 | 5.52 | 3.31 | 3.5 | 3.5 | 3.5 | 6.78 | 10.35 | 10.36 | 10.36 | 10.36 |
| Xanthan Gum | 0.43 | 0.42 | 0.25 | 0.26 | 0.26 | 0.26 | 0.3 | 0.78 | 0.82 | 0.82 | 0.82 |
| Antifoam | 2.52 | 2.46 | 1.48 | 1.56 | 1.56 | 1.56 | 3.09 | 4.61 | 4.59 | 4.59 | 4.59 |
| Na Sulfonate | 5.0 | 5.0 | 5.0 | 5.0 | 5.0 | 12.5 | 12.56 | 37.5 | 37.92 | 37.92 | 37.92 |
| Bactericide A | — | — | — | — | — | — | — | — | 0.59 | 0.59 | 0.59 |
| Isocyanate Solution | | | | | | | | | | | |
| Cadusafos | 140.0 | 140.0 | 140.0 | 140.0 | 140.0 | 137.86 | 136.5 | 409.5 | 409.5 | 409.5 | 409.5 |
| PMPPI | 12.0 | 15.0 | 25.0 | 10.0 | 15.0 | 15.0 | 15.0 | 60.0 | 45.0 | 45.0 | 90.0 |
| Cu naphthalene | 0.7 | 0.7 | 0.7 | 0.7 | 1.4 | 3.54 | 3.5 | 10.5 | 10.5 | 10.5 | 10.5 |

TABLE 1-continued

Preparation of Cadusafos Capsule Suspension (CS) Formulations
(Components and Amounts)

| Amine Solution | | | | | | | | | | |
|---|---|---|---|---|---|---|---|---|---|---|
| DETA | 7.6 | 9.5 | 15.2 | 6.1 | 9.5 | 3.8 | — | — | — | 28.5 | — |
| HDA | — | — | — | — | — | — | 6.51 | 26.04 | 19.5 | — | 39.06 |
| Water | 12.4 | 15.5 | 24.8 | 9.9 | 15.5 | 6.2 | 18.49 | 48.96 | 55.5 | 46.5 | 36.74 |
| Post Encapsulation Stabilizers | | | | | | | | | | |
| Propylene Glycol | 35.0 | 35.0 | 35.0 | 35.0 | 35.0 | 35.0 | 35.0 | 105.0 | 105.0 | 105.0 | 105.0 |
| Xanthan Gum | 0.7 | 0.7 | 0.7 | 0.7 | 0.5 | 0.5 | 0.5 | 1.5 | 1.5 | 1.5 | 1.5 |
| Water | 34.3 | 34.3 | 34.3 | 34.3 | 24.5 | 24.5 | 24.5 | 73.5 | 73.5 | 73.5 | 73.5 |
| Con. $H_3PO_4$ | — | — | — | — | — | — | 0.1 | 1.0 | — | 20.0 | — |
| Con. HCl | 12.0 | 12.0 | 17.0 | 17.0 | 12.0 | 0.6 | — | — | — | — | — |
| Na Sulfonate | 7.5 | 7.5 | 7.5 | 7.5 | 7.5 | — | — | — | — | — | — |
| Bactericide B | 0.3 | 0.3 | 0.3 | 0.3 | 0.3 | 0.3 | — | 1.0 | 1.0 | 1.0 | — |

| | Weight (grams) | | |
|---|---|---|---|
| Formulation (grams/L) | PP (200) | QQ (200) | RR (200) |
| Component | | | |
| Aqueous Solution | | | |
| Water | 327.85 | 327.85 | 607.15 |
| PVA | 3.06 | 3.06 | 5.63 |
| Xanthan Gum | 0.23 | 0.23 | 0.45 |
| Antifoam | 1.36 | 1.36 | 2.39 |
| Na sulfonate | — | — | 20.42 |
| Bactericide B | — | — | 0.21 |
| Isocyanate Solution | | | |
| Cadusafos | 136.5 | 136.5 | 221.63 |
| Cu naphthalene | 3.5 | 3.5 | 5.52 |
| Petroleum Solvent | 60.0 | — | — |
| Corn Oil | — | 60.0 | — |
| PMPPI | 43.0 | 43.0 | 40.64 |
| Amine Solution | | | |
| HDA | 18.9 | 18.9 | 25.11 |
| Water | 18.1 | 18.1 | 11.73 |
| Post Encapsulation Stabilizers | | | |
| Con. $H_3PO_4$ | — | — | 5.11 |
| Water | 24.5 | 24.5 | 39.98 |
| Xanthan Gum | 0.5 | 0.5 | 0.80 |
| Urea | 35.0 | 35.0 | 53.24 |
| Antifoam | 1.36 | 1.36 | 1.99 |
| Inert dye | — | — | 0.21 |

PVA - Airvol ® 203 polyvinyl alcohol
Xanthan gum - Kelzan ® M and Kelzane ® S xanthan gums differ in that S has been surface treated to improve ease of dispersion. M was used in preparing the aqueous solution for Formulations A to R while Formulations S to Z used S. The xanthan gum used in the post encapsulation stabilization was Kelzan ® S.
Antifoam - Dow Corning ® 1500 is 100% polydimethyl siloxane. Dow Corning ® 1520 is a 20% solution. 1500 was used in Formulations A and B; 1520 in all others.
Petroleum solvent - Aromatic 200 ND, a mixture of $C_9$–$C_{15}$ aromatic, naphthalene-depleted, hydrocarbons, flash-point 95° C., or Exxate ® 1000, an acetic acid, $C_9$–$C_{11}$ branched alkyl esters. Exxate 1000 was used in Formulation RR only.
PMPPI - polymethylene polyphenyl isocyanate, Mondur ® MR or Papi 27. Papi 27 was used for Formulation QQ while Mondur ® MR was used for the others.
TETA - triethylenetetramine; DETA - triethylenediamine; HDA - 1,6-hexanediamine
Na sulfonate - sodium alkyl naphthalene sulfonate, Lomar ® PW, Emery ® 5355, or Lomar ® LS-1. Formulations A to GG used Lomar PW, Formulation HH used Emery 5355, and Formulations JJ to ZZ used Lomar ® LS-1.
Bactericide A - mixture of 2-methyl-4-isothiazolin-3-ones, Legend ® MK; Bactericide B - 1,2 benzisothiazolin-3-one, Proxel ® GXL
Amphoteric Surfactant - sodium lauriminodipropionate, Mirataine ™ H2-C-HA
Inert dye - Tricon Green 18800

TABLE 2

Cadusafos Capsule Suspension (CS) Formulations
(Components and Weight/Weight Percents)

| Formulation | Percent (wt/wt) | | | | | | | | | |
|---|---|---|---|---|---|---|---|---|---|---|
| | A (240) | B (200) | C (180) | D (200) | E and E-2 | E-1 | F (200) | G (240) | H (220) | J (270) |
| Components | | | | | | | | | | |
| PVA | 0.58 | 0.58 | 0.56 | 0.67 | 0.58 | 0.58 | 0.63 | 0.66 | 0.64 | 0.66 |
| Xanthan Gum | 0.05 | 0.05 | 0.18 | 0.17 | 0.19 | 0.19 | 0.20 | 0.21 | 0.21 | 0.21 |
| Antifoam | 0.26 | 0.26 | 0.25 | 0.30 | 0.24 | 0.24 | 0.26 | 0.27 | 0.26 | 0.27 |
| Cadusafos | 24.49 | 20.35 | 19.58 | 23.43 | 20.49 | 20.50 | 22.00 | 23.13 | 22.57 | 23.13 |
| Petroleum Solvent | — | 4.36 | 4.20 | 5.02 | 4.39 | 4.39 | 4.71 | 4.96 | 4.84 | — |
| PMPPI | 5.19 | 4.36 | 4.20 | 5.02 | 4.39 | 4.39 | 2.36 | 1.24 | 1.93 | 4.96 |
| TETA | 2.74 | 2.76 | 2.66 | 3.18 | — | — | — | — | — | — |
| DETA | — | — | — | — | 2.78 | 2.78 | 1.49 | 0.78 | 1.16 | 1.40 |
| Propylene Glycol | — | — | 1.30 | 1.56 | 1.32 | 1.32 | 1.41 | 1.49 | 1.45 | 1.49 |
| Con. H$_3$PO$_4$ | — | — | 2.52 | — | 2.63 | 2.64 | 1.73 | — | 0.64 | — |
| Con. HCl | — | — | — | 2.59 | — | — | — | — | — | 1.97 |
| Na Sulfonate | — | — | — | — | 0.73 | 0.73 | 0.79 | 0.83 | 0.81 | 0.83 |
| Bactericide A | — | — | — | — | 0.04 | — | 0.05 | 0.05 | 0.05 | — |
| Water | 66.69 | 67.28 | 64.55 | 58.06 | 62.22 | 62.24 | 64.37 | 66.38 | 65.44 | 65.08 |
| Total | 100.00 | 100.00 | 100.00 | 100.00 | 100.00 | 100.00 | 100.00 | 100.00 | 100.00 | 100.00 |

| Formulation | Percent (wt/wt) | | | | | | | | | |
|---|---|---|---|---|---|---|---|---|---|---|
| | K (200) | L (240) | M (240) | N (240) | O (240) | P (250) | Q (250) | R (250) | S (250) | T (250) |
| Component | | | | | | | | | | |
| PVA | 0.47 | 0.47 | 1.58 | 1.59 | 0.52 | 0.45 | 0.41 | 0.47 | 0.41 | 0.41 |
| Xanthan Gum | 0.18 | 0.21 | 0.22 | 0.22 | 0.21 | 0.22 | 0.22 | 0.23 | 0.22 | 0.22 |
| Antifoam | 0.21 | 0.21 | 0.22 | 0.22 | 0.23 | 0.20 | 0.21 | 0.19 | 0.19 | 0.19 |
| Cadusafos | 20.54 | 25.03 | 25.21 | 25.40 | 29.25 | 26.08 | 25.80 | 26.88 | 25.99 | 25.99 |
| Petroleum Solvent | 4.40 | — | — | — | — | — | — | — | — | — |
| PMPPI | 4.40 | 2.68 | 2.70 | 2.72 | 2.58 | 2.79 | 4.42 | 2.88 | 4.46 | 4.46 |
| DETA | 2.79 | 1.79 | 1.71 | 1.72 | 1.63 | 1.77 | 2.87 | 1.09 | 2.68 | 2.68 |
| Propylene Glycol | 1.47 | 5.01 | 5.04 | 5.08 | 4.82 | 5.22 | 5.16 | 5.38 | 5.20 | 5.20 |
| Con. H$_3$PO$_4$ | 2.42 | 1.97 | 1.98 | 1.24 | 1.18 | 1.58 | 2.10 | 0.48 | 2.12 | 2.12 |
| Na Sulfonate | 0.73 | 0.89 | 0.90 | 0.91 | 0.86 | 0.93 | 0.92 | 0.96 | 0.74 | 0.74 |
| Bactericide A | 0.02 | 0.05 | 0.05 | 0.05 | 0.05 | 0.06 | 0.06 | 0.06 | 0.06 | 0.06 |
| Amphoteric | — | 2.68 | — | — | — | — | — | — | — | — |
| Water | 62.37 | 59.01 | 60.39 | 60.85 | 58.67 | 60.70 | 57.86 | 61.36 | 57.93 | 57.93 |
| Total | 100.00 | 100.00 | 100.00 | 100.00 | 100.00 | 100.00 | 100.00 | 100.00 | 100.00 | 100.00 |

| Formulation | Percent (wt/wt) | | | | | | | | | |
|---|---|---|---|---|---|---|---|---|---|---|
| | U (250) | V (250) | W-1 | W-2 | W-3 | X (250) | Y (250) | Z (250) | AA | BB | BB-1 |
| Component | | | | | | | | | | |
| PVA | 0.43 | 0.41 | 0.64 | 0.62 | 0.58 | 0.41 | 0.45 | 0.47 | 0.45 | 0.53 | 0.55 |
| Xanthan Gum | 0.13 | 0.22 | 0.09 | 0.09 | 0.09 | 0.22 | 0.17 | 0.13 | 0.17 | 0.15 | 0.15 |
| Cadusafos | 27.27 | 26.08 | 37.01 | 35.82 | 33.84 | 26.28 | 26.79 | 26.86 | 26.71 | 21.36 | 21.29 |
| Petroleum Solvent | — | — | 3.98 | 3.86 | 3.64 | — | — | — | — | — | — |
| PMPPI | 4.67 | 2.79 | 7.98 | 7.73 | 7.30 | 2.82 | 2.87 | 2.88 | 2.86 | 2.29 | 1.83 |
| Cu naphthalene | — | — | — | — | — | — | — | — | 0.27 | 0.11 | 0.11 |
| DETA | 2.81 | 1.77 | 3.19 | 3.09 | 2.92 | 1.78 | 1.82 | 1.82 | 1.81 | 1.45 | 0.06 |
| Propylene Glycol | 5.45 | 5.22 | — | — | 4.67 | 5.26 | 5.36 | 5.37 | 5.34 | 5.34 | 5.32 |
| Con. H$_3$PO$_4$ | 2.22 | 1.58 | — | — | — | — | — | — | — | — | — |
| Con. HCl | — | — | 2.04 | 1.98 | 1.87 | 4.13 | 2.26 | 2.00 | 2.29 | 1.83 | 1.83 |
| Na Sulfonate | 0.78 | 0.93 | 6.95 | 6.72 | 6.94 | 2.35 | 2.39 | 2.40 | 2.38 | 1.91 | 1.90 |
| Bactericide A | — | 0.06 | — | — | — | — | — | — | — | — | — |
| Bactericide B | — | — | — | — | 0.05 | 0.06 | 0.06 | 0.06 | 0.06 | 0.05 | 0.05 |
| Amphoteric | — | 4.66 | — | 3.21 | 3.04 | — | — | — | — | — | — |
| Antifoam | 0.19 | 0.18 | 0.29 | 0.28 | 0.50 | 0.18 | 0.20 | 0.21 | 0.20 | 0.24 | 0.24 |
| Water | 56.05 | 56.10 | 37.83 | 36.60 | 34.56 | 56.51 | 57.63 | 57.80 | 57.46 | 64.74 | 66.67 |
| Total | 100.00 | 100.00 | 100.00 | 100.00 | 100.00 | 100.00 | 100.00 | 100.00 | 100.00 | 100.00 | 100.00 |

TABLE 2-continued

Cadusafos Capsule Suspension (CS) Formulations
(Components and Weight/Weight Percents)

| Formulation | Percent (wt/wt) | | | | | | | | | | |
|---|---|---|---|---|---|---|---|---|---|---|---|
| | CC | DD | EE | FF (200) | GG | HH | JJ (200) | KK | LL (200) | MM | NN |
| Component | | | | | | | | | | | |
| PVA | 0.64 | 0.63 | 0.50 | 0.54 | 0.54 | 0.56 | 1.07 | 0.54 | 0.55 | 0.54 | 0.53 |
| Xanthan Gum | 0.13 | 0.13 | 0.14 | 0.15 | 0.12 | 0.12 | 0.13 | 0.12 | 0.12 | 0.12 | 0.12 |
| Antifoam | 0.29 | 0.28 | 0.22 | 0.24 | 0.24 | 0.25 | 0.49 | 0.24 | 0.24 | 0.24 | 0.24 |
| Cadusafos | 15.86 | 15.99 | 21.04 | 21.66 | 21.67 | 22.24 | 21.58 | 21.56 | 21.57 | 21.34 | 21.07 |
| PMPPI | 1.36 | 1.71 | 3.76 | 1.55 | 2.32 | 2.42 | 2.37 | 3.16 | 2.37 | 2.35 | 4.63 |
| Cu naphthalene | 0.08 | 0.08 | 0.11 | 0.11 | 0.22 | 0.57 | 0.55 | 0.55 | 0.55 | 0.55 | 0.54 |
| DETA | 0.86 | 1.09 | 2.28 | 0.94 | 1.47 | 0.61 | 0.00 | 0.00 | 0.00 | 1.49 | 0.00 |
| HDA | 0.00 | 0.00 | 0.00 | 0.00 | 0.00 | 0.00 | 1.03 | 1.37 | 1.03 | 0.00 | 2.01 |
| Propylene Glycol | 3.97 | 4.00 | 5.26 | 5.41 | 5.42 | 5.65 | 5.53 | 5.53 | 5.53 | 5.47 | 5.40 |
| Con. $H_3PO_4$ | 0.00 | 0.00 | 0.00 | 0.00 | 0.00 | 0.00 | 0.02 | 0.05 | 0.00 | 1.04 | 0.00 |
| Con. HCl | 1.36 | 1.37 | 2.55 | 2.63 | 1.86 | 0.10 | 0.00 | 0.00 | 0.00 | 0.00 | 0.00 |
| Na Sulfonate | 1.42 | 1.43 | 1.88 | 1.93 | 1.93 | 2.02 | 1.99 | 1.97 | 2.00 | 1.98 | 1.95 |
| Bactericide A | — | — | — | — | — | — | — | — | 0.03 | 0.03 | 0.03 |
| Bactericide B | 0.03 | 0.03 | 0.05 | 0.05 | 0.05 | 0.05 | — | 0.05 | 0.05 | 0.05 | — |
| Water | 74.00 | 73.26 | 62.21 | 64.79 | 64.16 | 65.41 | 65.24 | 64.86 | 65.96 | 64.80 | 63.48 |
| Total | 100.00 | 100.00 | 100.00 | 100.00 | 100.00 | 100.00 | 100.00 | 100.00 | 100.00 | 100.00 | 100.00 |

| Formulation (grams/L) | Percent (wt/wt) | | |
|---|---|---|---|
| | PP (200) | QQ (200) | RR (200) |
| Component | | | |
| PVA | 0.46 | 0.46 | 0.54 |
| Xanthan Gum | 0.11 | 0.11 | 0.12 |
| Antifoam | 0.20 | 0.20 | 0.42 |
| Cadusafos | 20.30 | 20.30 | 21.27 |
| Cu naphthalene | 0.52 | 0.52 | 0.53 |
| Petroleum Solvent | 8.92 | — | — |
| Corn Oil | — | 8.92 | — |
| PMPPI | 6.39 | 6.39 | 3.90 |
| HDA | 2.81 | 2.81 | 2.41 |
| Urea | 5.20 | 5.20 | 5.11 |
| Con. $H_3PO_4$ | — | — | 0.49 |
| Na sulfonate | — | — | 1.96 |
| Bactercide B | — | — | 0.02 |
| Inert dye | — | — | 0.02 |
| Water | 55.09 | 55.09 | 63.21 |
| Total | 100.00 | 100.00 | 100.00 |

TABLE 3

Large Scale Preparation of 200 grams/Liter Cadusafos CS Formulations
(Components and Amounts)
Weight (pounds)

| Formulation | PB-1 | PB-2 | PB-3 | PB-4 | PB-5PG | PB-5U | PB-6PG | PB-6U | PB-7PG | PB-7U |
|---|---|---|---|---|---|---|---|---|---|---|
| Component | | | | | | | | | | |
| Isocyanate Solution | | | | | | | | | | |
| Cadusafos | 189.2 | 165.8 | 165.8 | 113.7 | 83.3 | 82.6 | 83.3 | 82.6 | 83.3 | 82.6 |
| Cu Naphthenate | 4.7 | 4.1 | 4.1 | 2.8 | 2.1 | 2.1 | 2.1 | 2.1 | 2.1 | 2.1 |
| PMPPI | 24.0 | 24.0 | 24.0 | 25.0 | 9.1 | 9.1 | 9.1 | 9.1 | 12.2 | 12.1 |
| Aqueous Solution | | | | | | | | | | |
| Water | 449.0 | 449.3 | 454.6 | 454.6 | 229.2 | 227.3 | 229.4 | 227.6 | 225.3 | 223.6 |
| PVA | 4.14 | 4.14 | 4.22 | 4.22 | 2.11 | 2.09 | 2.11 | 2.09 | 2.08 | 2.06 |
| Xanthan Gum | 0.33 | 0.33 | 0.33 | 0.33 | 0.17 | 0.16 | 0.17 | 0.16 | 0.17 | 0.16 |
| Antifoam | 1.80 | 1.80 | 1.90 | 1.90 | 0.90 | 0.90 | 0.92 | 0.91 | 0.90 | 0.90 |
| Na sulfonate | 15.10 | 15.10 | 15.30 | 15.30 | 0.28 | 0.28 | 0.23 | 0.23 | 7.58 | 7.52 |
| Bactericide B | 0.15 | 0.15 | 0.15 | 0.15 | 0.07 | 0.07 | 0.07 | 0.07 | 0.07 | 0.07 |

TABLE 3-continued

Large Scale Preparation of 200 grams/Liter Cadusafos CS Formulations
(Components and Amounts)

| Amine Solution | | | | | | | | | | |
|---|---|---|---|---|---|---|---|---|---|---|
| HDA | 10.5 | 10.5 | 13.2 | 15.8 | — | — | — | — | 5.3 | 5.2 |
| DETA | — | — | — | — | 5.8 | 5.7 | 5.8 | 5.7 | — | — |
| Water | 19.7 | 19.7 | 13.7 | 14.9 | 9.4 | 9.4 | 9.4 | 9.4 | 9.9 | 9.8 |
| Post Encapsulation Additives | | | | | | | | | | |
| Con. $H_3PO_4$ | 2.9 | 4.3 | 3.7 | 7.4 | 3.5 | 3.4 | 3.5 | 3.4 | 1.2 | 1.2 |
| Water | 0.5 | 0.8 | 0.7 | 1.3 | 0.6 | 0.6 | 0.6 | 0.6 | 0.2 | 0.2 |
| Xanthan Gum | 0.59 | 0.61 | 0.86 | 0.61 | 0.30 | 0.30 | 0.30 | 0.30 | 0.30 | 0.30 |
| Water | 29.0 | 29.9 | 42.2 | 29.9 | 14.9 | 14.8 | 14.7 | 14.8 | 14.7 | 14.7 |
| Propylene glycol | 42.5 | 42.5 | 42.5 | 42.5 | 21.0 | — | 21.0 | — | 22.0 | — |
| Urea | — | — | — | — | — | 20.0 | — | 20.0 | — | 20.0 |
| Bactericide B | 0.27 | 0.27 | 0.39 | 0.27 | 0.14 | — | 0.14 | — | 0.14 | 0.14 |
| Antifoam | 1.56 | 1.56 | 1.56 | 1.56 | — | — | — | — | 0.78 | |

| | Weight (pounds) | | | | | | | | | |
|---|---|---|---|---|---|---|---|---|---|---|
| Formulation | PB-8PG | PB-8U | PB-9PG | PB-9U | PB-11PG | PB-11U | PB-I2PG | PB-12U | PB-13U-ND | PB-C14U-ND | PB-C18U |
| Component | | | | | | | | | | | |
| Isocyanate Solution | | | | | | | | | | | |
| Isocyanate Solution | | | | | | | | | | | |
| Cadusafos | 82.6 | 83.2 | 81.9 | 83.9 | 82.6 | 83.2 | 83.3 | 82.6 | 165.8 | 172.6 | 1254.68 |
| Cu Naphthenate | 2.1 | 2.1 | 2.0 | 2.1 | 2.1 | 2.1 | 2.1 | 2.1 | 4.1 | 4.21 | — |
| PMPPI | 15.1 | 15.3 | 18.0 | 18.5 | 15.1 | 15.3 | 9.1 | 9.1 | 56.5 | 53.0 | 386.86 |
| Petroleum Solvent | — | — | — | — | — | — | — | — | 73.0 | 74.1 | 538.47 |
| Aqueous Solution | | | | | | | | | | | |
| Aqueous Solution | | | | | | | | | | | |
| Water | 226.2 | 227.8 | 224.2 | 229.8 | 234.1 | 235.7 | 227.9 | 226.1 | 397.9 | 391.3 | 2795.06 |
| PVA | 2.09 | 2.11 | 2.07 | 2.13 | 2.09 | 2.11 | 2.1 | 2.1 | 3.7 | 7.24 | 51.71 |
| Xanthan Gum | 0.16 | 0.17 | 0.16 | 0.17 | 0.15 | 0.15 | 0.2 | 0.2 | 0.26 | 0.32 | 2.27 |
| Antifoam | 0.90 | 0.90 | 0.89 | 0.91 | 0.91 | 0.91 | 0.9 | 0.9 | 1.8 | 3.33 | 23.76 |
| Na sulfonate | 7.62 | 7.68 | 7.56 | 7.74 | 7.62 | 7.68 | 7.7 | 7.6 | — | 7.53 | 53.6 |
| Bactericide B | 0.07 | 0.07 | 0.07 | 0.08 | 0.05 | 0.05 | 0.1 | 0.1 | — | 0.20 | 1.4 |
| Amine Solution | | | | | | | | | | | |
| Amine Solution | | | | | | | | | | | |
| HDA | 6.6 | 6.6 | 7.8 | 8.0 | 6.6 | 6.6 | 4.0 | 3.9 | 32.8 | 33.3 | 166.52 |
| DETA | — | — | — | — | — | — | — | — | — | — | — |
| Water | 7.2 | 7.2 | 7.3 | 7.5 | 6.8 | 6.9 | 11.1 | 11.0 | 12.1 | 12.3 | 159.48 |
| Post Encapsulation Additives | | | | | | | | | | | |
| Post Encapsulation | | | | | | | | | | | |
| Con. $H_3PO_4$ | 1.9 | 1.9 | 2.1 | 2.1 | 1.9 | 1.9 | 1.7 | 1.7 | 4.2 | 6.34 | 63.75 |
| Water | 0.3 | 0.3 | 0.4 | 0.4 | 0.3 | 0.3 | 0.3 | 0.3 | 0.8 | 1.13 | 11.25 |
| Xanthan Gum | 0.31 | 0.3 | 0.31 | 0.30 | 0.3 | 0.31 | 0.31 | 0.3 | 0.61 | 0.64 | 4.6 |
| Water | 15.2 | 14.7 | 15.2 | 14.7 | 14.7 | 15.2 | 15.2 | 14.7 | 29.9 | 31.4 | 226.0 |
| Propylene glycol | 22.0 | — | 22.0 | — | 20.0 | — | 22.0 | — | — | — | — |
| Urea | — | 20.0 | — | 20.0 | — | 22.0 | — | 20.0 | 42.5 | 44.6 | 321.6 |
| Bactericide B | 0.14 | 0.14 | 0.14 | 0.14 | — | — | — | — | — | — | — |
| Antifoam | 0.81 | 0.75 | 0.81 | 0.75 | 0.76 | 0.8 | 0.8 | 0.8 | — | — | — |
| Inert dye | — | — | — | — | — | — | — | — | — | 0.17 | 1.3 |

TABLE 4

Large Scale Preparation of 200 grams/Liter Cadusafos CS Formulations (Components and Weight/Weight Percents)

| Formulation (grams/L) | Percent (wt/wt) | | | | | | | | | |
|---|---|---|---|---|---|---|---|---|---|---|
| | PB-1 | PB-2 | PB-3 | PB-4 | PB-5PG | PB-5U | PB-6PG | PB-6U | PB-7PG | PB-7U |
| Component | | | | | | | | | | |
| Cadusafos | 23.77 | 21.4 | 21.01 | 15.38 | 21.75 | 21.8 | 21.75 | 21.79 | 21.44 | 21.55 |
| Copper Napthenate | 0.59 | 0.54 | 0.53 | 0.39 | 0.54 | 0.55 | 0.54 | 0.55 | 0.54 | 0.54 |
| PMPPI | 3.01 | 3.10 | 3.04 | 3.41 | 2.39 | 2.39 | 2.39 | 2.39 | 3.14 | 3.16 |
| PVA | 0.52 | 0.53 | 0.53 | 0.58 | 0.55 | 0.55 | 0.55 | 0.55 | 0.54 | 0.54 |
| Xanthan Gum | 0.12 | 0.12 | 0.15 | 0.13 | 0.12 | 0.12 | 0.12 | 0.12 | 0.12 | 0.12 |
| Antifoam | 0.42 | 0.43 | 0.44 | 0.47 | 0.24 | 0.24 | 0.24 | 0.24 | 0.43 | 0.44 |
| HDA | 1.32 | 1.35 | 1.67 | 2.16 | — | — | — | — | 1.36 | 1.36 |
| DETA | — | — | — | — | 1.51 | 1.51 | 1.51 | 1.51 | — | — |
| Propylene glycol | 5.34 | 5.48 | 5.38 | 5.80 | 5.49 | — | 5.49 | — | 5.67 | — |
| Urea | — | — | — | — | — | 5.28 | — | 5.28 | — | 5.22 |
| Con. $H_3PO_4$ | 0.36 | 0.56 | 0.47 | 1.01 | 0.90 | 0.91 | 0.90 | 0.90 | 0.32 | 0.32 |
| Na sulfonate | 1.90 | 1.95 | 1.94 | 2.09 | 0.07 | 0.07 | 0.06 | 0.06 | 1.95 | 1.96 |
| Bactericide B | 0.05 | 0.05 | 0.07 | 0.06 | 0.06 | 0.02 | 0.05 | 0.02 | 0.05 | 0.02 |
| Water | 62.60 | 64.49 | 64.77 | 68.38 | 66.38 | 66.56 | 66.40 | 66.59 | 64.44 | 64.75 |
| Total | 100.00 | 100.00 | 100.00 | 100.00 | 100.00 | 100.00 | 100.00 | 100.00 | 100.00 | 100.00 |

| Formulation (grams/L) | Percent (wt/wt) | | | | | | | | | |
|---|---|---|---|---|---|---|---|---|---|---|
| | PB-8PG | PB-8U | PB-9PG | PB-9U | PB-11PG | PB-11U | PB-12PG | PB-12U | PB-13U-ND | PB-C14U-ND | PB-C18U |
| Component | | | | | | | | | | | |
| Component | | | | | | | | | | | |
| Cadusafos | 21.11 | 21.27 | 20.84 | 21.03 | 20.86 | 20.74 | 21.42 | 21.54 | 20.08 | 20.46 | 20.7 |
| Copper Naphthenate | 0.53 | 0.53 | 0.52 | 0.53 | 0.52 | 0.52 | 0.54 | 0.54 | 0.50 | 0.50 | — |
| PMPPI | 3.87 | 3.90 | 4.59 | 4.63 | 3.82 | 3.80 | 2.35 | 2.36 | 6.84 | 6.28 | 6.38 |
| Petroleum Solvent | — | — | — | — | — | — | — | — | 8.84 | 8.78 | 8.88 |
| PVA | 0.53 | 0.54 | 0.53 | 0.53 | 0.53 | 0.53 | 0.54 | 0.55 | 0.45 | 0.86 | 0.85 |
| Xanthan Gum | 0.12 | 0.12 | 0.12 | 0.12 | 0.11 | 0.11 | 0.12 | 0.12 | 0.11 | 0.11 | 0.04 |
| Antifoam | 0.44 | 0.42 | 0.43 | 0.42 | 0.42 | 0.43 | 0.44 | 0.44 | 0.22 | 0.39 | 0.39 |
| HDA | 1.68 | 1.69 | 1.99 | 2.01 | 1.65 | 1.65 | 1.02 | 1.03 | 3.97 | 3.95 | 3.92 |
| Propylene glycol | 5.62 | — | 5.60 | — | 5.05 | — | 5.66 | — | — | — | — |
| Urea | — | 5.11 | — | 5.01 | — | 5.48 | — | 5.22 | 5.14 | 5.29 | 5.30 |
| Con. $H_3PO_4$ | 0.49 | 0.49 | 0.53 | 0.54 | 0.48 | 0.48 | 0.44 | 0.44 | 0.51 | 0.76 | 1.24 |
| Nasulfonate | 1.95 | 1.96 | 1.92 | 1.94 | 1.92 | 1.91 | 1.99 | 1.99 | — | 0.89 | 0.89 |
| Bactericide B | 0.05 | 0.05 | 0.05 | 0.05 | 0.01 | 0.01 | 0.02 | 0.02 | — | 0.02 | 0.02 |
| Inert dye | — | — | — | — | — | — | — | — | — | 0.02 | 0.02 |
| Water | 63.61 | 63.92 | 62.88 | 63.19 | 64.63 | 64.34 | 65.46 | 65.75 | 53.34 | 51.69 | 51.37 |
| Total | 100.00 | 100.00 | 100.00 | 100.00 | 100.00 | 100.00 | 100.00 | 100.00 | 100.00 | 100.00 | 100.00 |

TABLE 5

Acute Mammalian Dermal Toxicity of Cadusafos CS Formulations

| Formulation | $LD_{50}$ (mg/kg) | Probable EPA Category |
|---|---|---|
| B | >1000 | II |
| F | >2000 and <5000 | II |
| G | >200 and <2000 | II |
| K | >2000 | III |
| KK | >2000 | III |
| LL[1] | >2000 | III |
| MM | >2000 | III |
| PB-8PG[1] | <2000 | II |
| PB-8U | <2000 | — |
| PB-9PG | >2000 | III |
| PB-11PG | >2000 | III |
| PB-12PG | >400 and <2000 | II |
| PB-C14U-ND | >5000 | IV |

[1]Formulation tested twice

The rat acute dermal toxicity $LD_{50}$ of a known cadusafos 100 ME formulation is 761 mg/kg, or Category II.

TABLE 6

Acute Mammalian Oral Toxicity of Cadusafos CS Formulations

| Formulation | $LD_{50}$ (mg/kg) | Probable EPA Category |
|---|---|---|
| B | >500 | III |

TABLE 6-continued

Acute Mammalian Oral Toxicity of Cadusafos CS Formulations

| Formulation | LD$_{50}$ (mg/kg) | Probable EPA Category |
|---|---|---|
| G | >50 and <500 | II |
| PP[1] | >500 | III |
| QQ | >500 | III |
| PB-8PG | <500 | — |
| PB-8U | <500 | — |
| PB-9PG | >200 and <500 | II |
| PB-11PG | >50 and <200[2] | II |
| PB-12PG | >50 and <200[2] | II |
| PB-C14U-ND | >506 and <5,000 | III |

[1] Formulation tested twice.
[2] Toxicity based on more sensitive female sex.
The rat acute oral toxicity LD$_{50}$ of a known cadusafos 100 ME formulation is 371 mg/kg, or Category II.

TABLE 7

Mean Rating of root galls caused by root-knot nematode, *M. incognita*, on tomatoes 48 hours after treatment with the Cadusafos CS Formulations
Mean Root-Knot Gall Rating

| Rate (Kg/Ha) Formulation | 0.25 | 0.5 |
|---|---|---|
| AA | 0 | 0 |
| BB | 0.8 | 0 |
| BB-1 | 1.8 | 0 |
| CC | 0.4 | 0 |
| EE | 0 | 0 |
| FF | 0.2 | 0 |
| 100 ME | 0 | 0 |
| Technical | 2.4 | 1.2 |

TABLE 8

Mean Rating of root galls caused by root-knot nematode, *M. incognita*, on tomatoes treated with the Cadusafos CS Formulations seven days prior to soil infestation with nematodes
Mean Root-Knot Gall Rating

| Rate(Kg/Ha) Formulation | 0.25 | 0.5 | 1.0 | 2.0 |
|---|---|---|---|---|
| AA | 1.2 | 0 | 0 | 0 |
| BB | 0.8 | 0 | 0 | 0 |
| BB-1 | 0.6 | 0.2 | 0 | 0 |
| CC | 0.8 | 0 | 0 | 0 |
| EE | 0.6 | 0 | 0 | 0 |
| FF | 0.8 | 0 | 0 | 0 |
| 100 ME | 0 | 0 | 0 | 0 |
| Technical | 4.4 | 3.0 | 0.6 | 0.4 |

1 Gall rating: 0 no galls, 10 is intense galling.

TABLE 9

Residual Soil Activity of Cadusafos CS formulations against Southern Corn Rootworm larvae in clay loam soil Residual Period (days)
Percent Mortality

| Formulation | rate (ppm) | 0 | 1 | 4 | 7 | 14 | 21 | 35 | 42 | 63 | 84 |
|---|---|---|---|---|---|---|---|---|---|---|---|
| B | 0.2 | 63 | 72 | 75 | 47 | 78 | 89 | 47 | 35 | 49 | — |
| E | 0.2 | 77 | 33 | 55 | 43 | 75 | 60 | 51 | 30 | 35 | 9 |
| F | 0.2 | 90 | 98 | 92 | 63 | 88 | 78 | 33 | 68 | 33 | — |
| G | 0.2 | 98 | 98 | 85 | 60 | 95 | 96 | 75 | 52 | 75 | 97 |
| H | 0.2 | 100 | 82 | 60 | 63 | 83 | 73 | 47 | 42 | 22 | — |
| PB-C14U-ND | 0.2 | — | 3 | 23 | 23 | 30 | 28 | — | — | — | — |
| 100 ME | 0.2 | 93 | 92 | 83 | 67 | 78 | 85 | 49 | 30 | 31 | 40 |
| Biodac 10G | 0.2 | — | 14 | 55 | 15 | 5 | 30 | — | — | — | — |

TABLE 10

Residual Soil Activity of Cadusafos CS formulations against Southern Corn Rootworm larvae in sandy loam soil Residual period (days)
Percent Mortality

| Formulation | rate (ppm) | 0 | 1 | 4 | 7 | 21 | 35 | 49 | 70 | 84 | 112 |
|---|---|---|---|---|---|---|---|---|---|---|---|
| B | 1.5 | 100 | 100 | 100 | 97 | 97 | 98 | 98 | 97 | 100 | 62 |
| E | 1.5 | 100 | 100 | 100 | 100 | 100 | 98 | 100 | 100 | 100 | 70 |
| F | 1.5 | 100 | 100 | 100 | 97 | 97 | 98 | 98 | 97 | 100 | 62 |
| G | 1.5 | 100 | 100 | 100 | 97 | 100 | 98 | 100 | 100 | 100 | 75 |
| H | 1.5 | 100 | 100 | 100 | 100 | 97 | 98 | 100 | 100 | 100 | 73 |
| 100 ME | 1.5 | 100 | 100 | 100 | 100 | 100 | 100 | 100 | 100 | 100 | 33 |

We claim:

1. A pestidical formulation prepared according to a process comprising the steps of:
   a) providing an aqueous phase containing one or more emulsifiers and an antifoam agent;
   b) providing a water-immiscible phase, said water-immiscible phase comprising cadusafos and an isocyanate monomer;
   c) emulsifying the water-immiscible phase in the aqueous phase forming a dispersion of water-immiscible droplets in the aqueous phase; and
   d) adding to the dispersion an aqueous solution of one or more polyfunctional amines, in an amount effective to achieve interfacial polymerization with the isocyanate monomer, thereby forming microencapsules of cadusafos having reduced mammalian toxicity as compared with known aqueous microemulsion cadusafos formulations of an equivalent or lesser cadusafos concentration.

2. A pesticidal formulation prepared according to a process comprising the steps of:
   (a) providing an aqueous phase comprised of the one or more emulsifiers and an antifoam agent, and optionally, a xanthan gum viscosity modifier/stabilizer and, optionally, a bactericide;
   (b) providing a water-immiscible phase comprised of cadusafos optionally pre-treated with a copper salt, polymethylene polyphenyl isocyanate and, optionally, a hydrocarbon solvent;
   (c) emulsifying the water-immiscible phase in the aqueous phase, forming a dispersion of water-immiscible droplets throughout the aqueous phase;
   (d) agitating the dispersion while adding thereto an aqueous solution comprised of one or more polyfunctional amines;
   (e) curing the microcapsules by continuing the agitation while heating the dispersion; and
   f) optionally, neutralizing the pH of the formulation with an acid.

3. A pesticidal formulation of cadusafos comprising an aqueous suspension of microcapsules, the microcapsules comprising a polyurea shell surrounding a core of the cadusafos, the polyurea shell having been formed from interfacial polymerization of an isocyanate and one or more polyfunctional amines, the polyurea shell being sufficiently impermeable to the cadusafos so as to effect a reduction in mammalian toxicity of the formulation as compared with aqueous microemulsion formulations having an equivalent or lesser cadusafos concentration.

4. The pesticidal formulation of claim 3, wherein said pesticidal formulation comprises the aqueous suspension of microcapules and contains from about 150 to about 360 grams of cadusafos per liter of formulation.

5. The pesticidal formulation of claim 3, comprising about 200 grams of cadusafos per liter of formulation.

6. The pesticidal formulation of claim 3, wherein the isocyanate is polymethylene polyphenyl isocyanate (PMPPI).

7. The pesticidal formulation of claim 3, wherein the polyfunctional amine is selected from the group consisting of diethylenetriamine, triethylenetetramine, 1,6-hexanediamine, and a combination of one or more of diethylenetriamine, triethylenetetramine, and 1,6-hexanediamine.

8. The pesticidal formulation of claim 3, which further comprises optionally, about 0.06 to about 0.4 weight percent of xanthan gum viscosity modifier/stabilizer; optionally, about 0.03 to about 0.05 of one or more bactericides; optionally, about 0.7 to about 6.7 weight percent of one or more surfactants; and optionally, about 1.2 to about 5.8 weight percent of propylene glycol or urea; said weight percents being based on the weight of the total formulation.

9. A granular pesticidal formulation of cadusafos, comprising carrier particles coated with the microcapsules of claim 3.

10. The granular formulation of claim 9, comprising about 5 to about 30 weight percent microcapsules, about 60 to about 95 weight percent carrier, and about 0.05 to about 5.0 weight percent of an adhesive agent; said weight percents being based on the weight of the total formulation.

11. A pesticidal formulation of from about 150 to about 360 grams cadusafos per liter of formulation, about 0.7 to about 2.5 weight percent polyvinyl alcohol and about 0.3 to about 0.9 weight percent of an antifoam agent, the formulation comprising an aqueous suspension of microcapsules, the microcapsules comprising a polyurea shell surrounding a core of the cadusafos, the polyurea shell having been formed from interfacial polymerization polymethylene polyphenyl isocyanate and one or more polyfunctional amines, wherein the weight percent of cadusafos is about 53 to about 92 percent of a water-immiscible phase provided for the interfacial polymerization, the weight percent of the polymethylene polyphenyl isocyanate is about 4 to about 25 percent of the water-immiscible phase, the polyfunctional amine is selected from the group consisting of diethylenetriamine, triethylenetetramine, 1,6-hexanediamine, and a combination of one or more of diethylenetriamine, triethylenetetramine, and 1,6-hexanediamine, the weight percent of the polyvinyl alcohol and antifoam agent are based on the total composition of the formulation with water included, and said formulation has reduced mammalian toxicity as compared with known aqueous microemulsion cadusafos formulations of an equivalent or lesser cadusafos concentration.

12. A pestidical formulation of cadusafos, comprising carrier particles coated with an aqueous pesticidal formulation of from about 150 to about 360 grams cadusafos per liter of aqueous formulation, about 0.7 to about 2.5 weight percent polyvinyl alcohol and about 0.3 to about 0.9 weight percent of an antifoam agent, the aqueous formulation comprising an aqueous suspension of microcapsules, the microcapsules comprising a polyurea shell surrounding a core of the cadusafos, the polyurea shell having been formed from interfacial polymerization of polymethylene polyphenyl isocyanate and one or more polyfunctional amines, wherein the weight percent of cadusafos is about 53 to about 92 percent of a water-immiscible phase provided for the interfacial polymerization, the weight percent of the polymethylene polyphenyl isocyanate is about 4 to about 25 percent of the water-immiscible phase, the polyfunctional amine is selected from the group consisting of diethylenetriamine, triethylenetetramine, 1,6-hexanediamine, and a combination of one or more of diethylenetriamine, triethylenetetramine, and 1,6-hexanediamine, the weight percent of the polyvinyl alcohol and antifoam agent are based on the total composition of the aqueous formulation with water included, and said aqueous formulation has reduced mammalian toxicity as compared with known aqueous microemulsion cadusafos formulations of an equivalent or lesser cadusafos concentration.

13. The pesticidal formulation of claim 11, wherein the weight percent of cadusafos is up to 98 weight percent of the water-immiscible phase and-the weight percent of the first polyfunctional amine is about 2 to 35 weight percent of the water-immiscible phase.

14. The pesticidal formulation of claim 2, wherein
   a) the weight percent of the one or more emulsifiers is about 0.3 to about 5.0 weight percent of the aqueous phase; the weight percent of the antifoam agent is about 0.1 to about 1.0 weight percent of the aqueous phase; the weight percent of the xanthan gum viscosity modifier/stabilizer, if any is used, is about 0.05 to about 0.50 weight percent of the aqueous phase; and the weight percent of the bactericide, if any is used, is about 0.02 to about 0.1 weight percent of the aqueous phase;
   b) the weight percent of cadusafos is about 50 to about 98 weight percent of the water-immiscible phase; the weight percent of the polymethylene polyphenyl isocyanate cadusafos is about 2 to about 35 weight percent of the water-immiscible phase; and the weight percent of the hydrocarbon solvent, if any is used, is about 15 to about 30 weight percent of the water-immiscible phase;
   c) the weight percent of the one or more polyfunctional amines is about 10 to about 100 weight percent of the aqueous solution; and
   d) the dispersion is heated at a temperature in the range of about 20 to about 60° C. for one to ten hours.

15. The pesticidal formulation of claim 14, wherein the one or more emulsifiers is polyvinyl alcohol and the weight percent of the polyvinyl alcohol is about 0.7 to about 2.5 weight percent of the aqueous phase; the weight percent of the antifoam agent is about 0.3 to about 0.9 weight percent of the aqueous phase; the weight percent of cadusafos is about 53 to about 92 weight percent of the water immiscible phase; the weight percent of the isocyanate is about 4 to about 25 percent of the water-immiscible phase; and the weight percent of the hydrocarbon solvent, if any is used, is about 20 to about 25 percent of the water immiscible phase.

16. A granular pesticide formulation of cadusafos prepared according to a process comprising drying the coated carrier particles of claim 12.

* * * * *

UNITED STATES PATENT AND TRADEMARK OFFICE
CERTIFICATE OF CORRECTION

PATENT NO. : 6,440,443 B1
DATED : August 27, 2002
INVENTOR(S) : Fui-Tseng H. Lee et al.

It is certified that error appears in the above-identified patent and that said Letters Patent is hereby corrected as shown below:

Column 28,
Line 65, "claim 11" should be -- claim 1 --

Signed and Sealed this

Twentieth Day of May, 2003

JAMES E. ROGAN
*Director of the United States Patent and Trademark Office*